United States Patent [19]

Frain

[11] 4,453,540
[45] Jun. 12, 1984

[54] POSITIONING STRUCTURE FOR HANDICAPPED PERSON

[75] Inventor: Joan M. Frain, Arlington, Va.

[73] Assignee: D.C. Society for Crippled Children, Inc., Washington, D.C.

[21] Appl. No.: 430,958

[22] Filed: Sep. 30, 1982

[51] Int. Cl.³ .............................................. A61F 13/00
[52] U.S. Cl. ..................................... 128/134; 269/328
[58] Field of Search ...................... 128/134, 83, 87, 69; 269/328; 5/81 R, 81 B, 82 R, 93

[56] References Cited

U.S. PATENT DOCUMENTS

| | | | |
|---|---|---|---|
| 3,729,752 | 5/1973 | Huggins | 128/134 |
| 3,854,156 | 12/1974 | Williams | 128/134 |
| 4,301,791 | 11/1981 | Franco | 128/134 |

Primary Examiner—John D. Yasko
Attorney, Agent, or Firm—Raymond N. Baker

[57] ABSTRACT

Custodial protective structure for severely handicapped children subject to involuntary spastic responses is disclosed. A body support, formed from an elastically resilient material such as foamed rubber or vinyl, provides a body mold cavity establishing relaxed positional support and provides limited yielding in the event of seizure. A stabilizer holds the body support to limit longitudinal yielding and prevent asymmetric twisting of the body support while allowing access for handling and therapy; the stabilizer framework facilitates canting of the structure or mounting for swinging movement.

4 Claims, 7 Drawing Figures

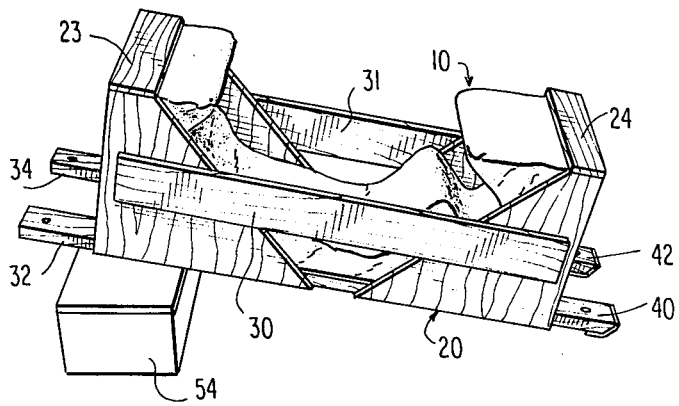
FIG.4
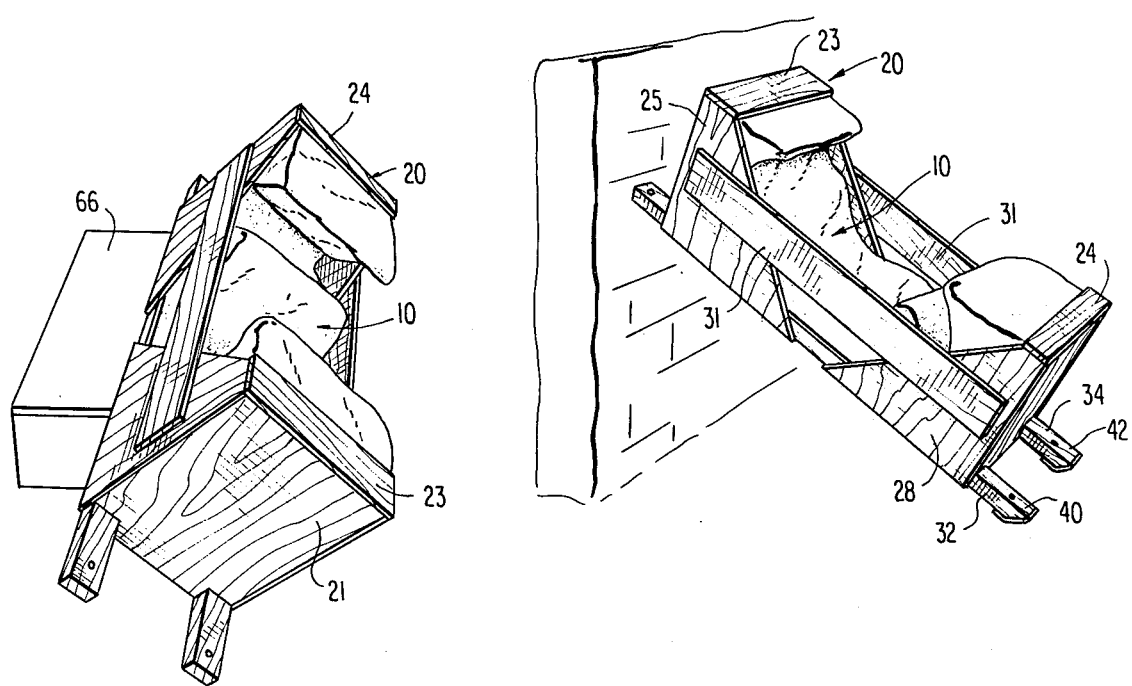
FIG.5
FIG.6
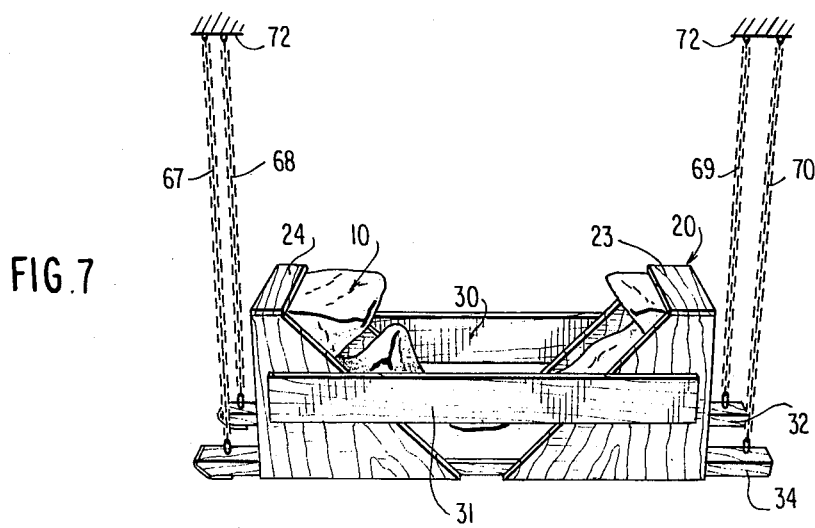
FIG.7

POSITIONING STRUCTURE FOR HANDICAPPED PERSON

This invention is concerned with means for facilitating positioning and application of therapeutic regimen to handicapped persons; in particular, profoundly handicapped infants and young children subject to involuntary reflex responses, such as opisthotonus or other manifestations of which are extensor thrust, associated with cerebral palsy.

The difficulties associated with handling and otherwise helping a child with profound nervous system disorders due to cerebral palsy damage in early childhood have been long recognized. At certain times, a parent, therapist, or other medical attendant must deal with the difficulties associated with the total helplessness of such a child, that is inability to hold the head or maintain any portion of the body against the pull of gravity, coupled with involuntary fluctuation of muscle tone. Such involuntary fluctuations for those with the named type of nervous system disorders can result from even slight changes in environmental conditions such as entry of a person into a room or abrupt changes in light level; and can lead to serious immediate problems which can contribute long-term detriment to the individual.

When such changes in environment conditions occur the child may go into an uncontrolled extensor thrust; i.e. a rigid arching of the body with head and neck back, toes pointed rearwardly and downwardly, and arms and shoulders extended rearwardly.

For further background, see, for example, the text "Handling the Young Cerebral Palsy Child at Home" by Nancie Finnie with foreword to 1st Edition by Dr. K. Bobath and Mrs. B. Bobath, 1975, published by E. P. Dutton, with special reference to pages IX–Xi, pages 1, 32, 33, 39–67.

As pointed out in the foreword of that text, "The treatment and management of children suffering from cerebral palsy requires the combined efforts of doctor, therapist, and parent." Also, as is clear from Chapter 4 of such text, little, if any, physical aids to help carry out basic feeding, handling and therapy, when working with a small child subject to these involuntary reflex responses, have not been available.

The present invention provides custodial and protective structure enabling an individual to handle and render therapeutic and other aids to a profoundly handicapped child while avoiding or substantially minimizing opportunity for such involuntary responses; and, further enabling positioning of the child in various selected positions to facilitate therapy or other basic assistance measures for the child.

More specific advantages and contributions of the invention will be considered in a more detailed description of an embodiment of the invention shown in the accompanying drawings. In these drawings.

Figure 1:
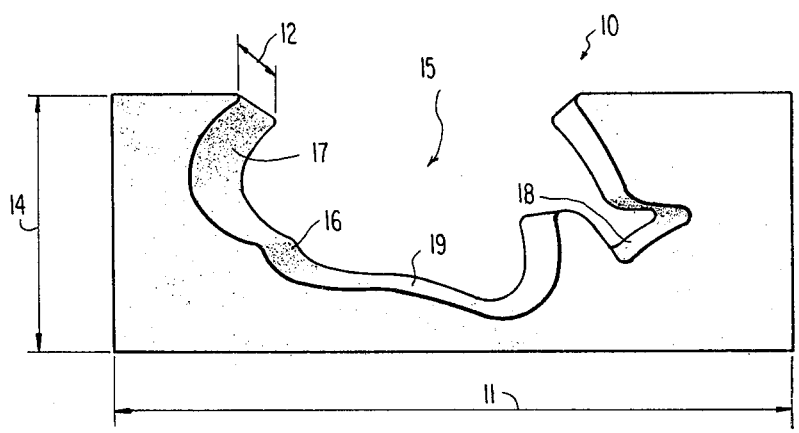
FIG. 1 is a perspective view of yieldable support with body cavity forming part of the present invention.
Figure 2:
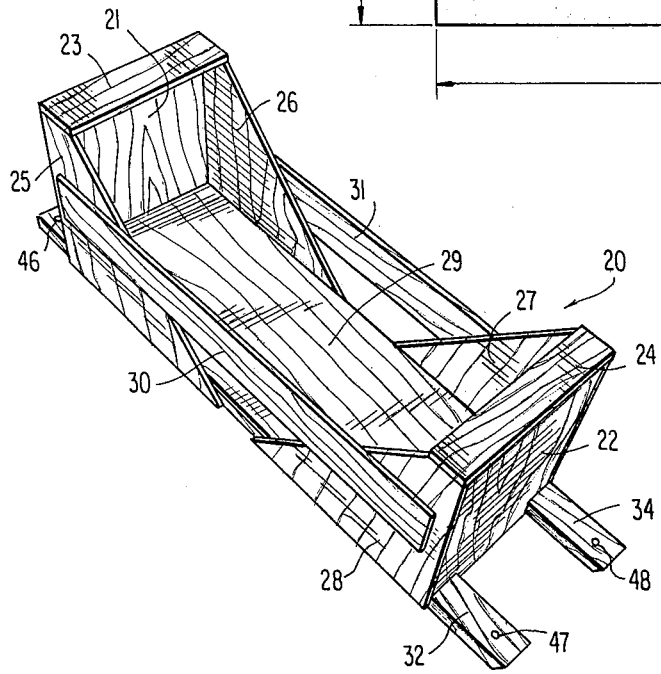
FIG. 2 is a perspective top-side view of stablizer means embodying the invention.
Figure 3:
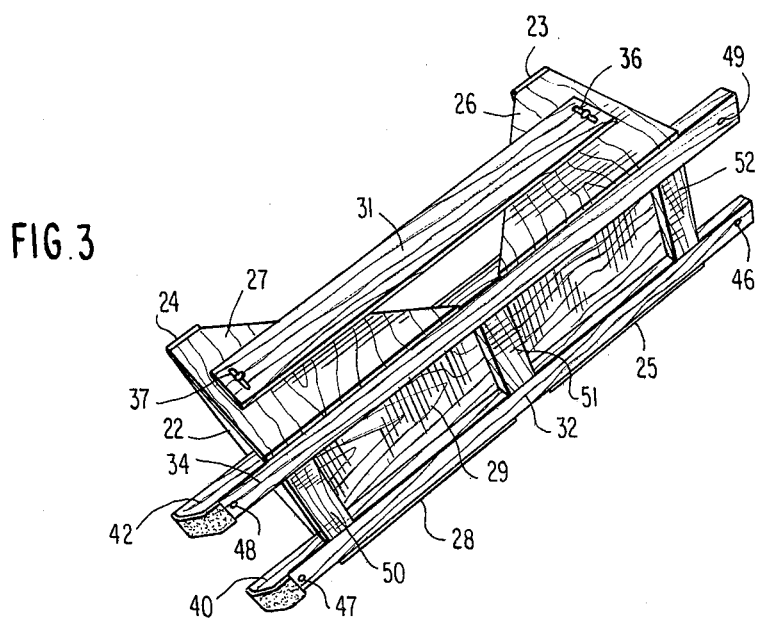
FIG. 3 is a perspective side-bottom view of the stabilizer means shown in FIG. 2.

FIGS. 4, 5 and 6 are perspective views of various canted positions for the combined body support of FIG. 1 and stabilizing means of FIGS. 2 and 3, and FIG. 7 is a view of the body support of FIG. 1 and stabilizing means of FIGS. 2 and 3 in combination with frame and connector means for providing swinging movement. The elongated yieldable body support 10 of FIG. 1 is formed from an elastically resiliant material, such as foam rubber or foam vinyl of selected density, to provide desired positioning for a patient and yieldable support. The longitudinal dimension 11, the width dimension 12, and depth dimension 14 are selected to accommodate the body size of the individual. Yieldable support 10 defines a body cavity 15 which positions an infant for body support longitudinally, i.e. supporting head, back, feet, and portions of the legs; and in a relaxed position, i.e. with the body arched slightly toward a fetal position, as shown. At shoulder level 16, the body support is concave in configuration to support the shoulders of a patient in slightly rounded position to minimize shoulder retraction while in the body mold cavity. The body support 10 includes a head portion 17, a foot portion 18 and a back portion 19.

An important contribution of the invention relates to means for properly restraining an infant while allowing for limited elastic yielding of the flexible body support. The invention also provides for use of such body support means in various positions and environments.

Referring to FIG. 2, a stabilizing means 20 includes end walls 21 and 22 which limit longitudinal expansion. In addition to end walls 21 and 22, top enclosure means at longitudinal ends of the body support can include cross-pieces 23 and 24. In the embodiment shown, side wall means 25, 26, 27, and 28 have a trapezoid shape extending downwardly from a full-depth position near longitudinal ends toward bottom support wall 29; this shape provides necessary holding for the body support 10 while allowing access, centrally of the structure, to an infant within the body support.

Lateral bracing members 30 and 31 extend directionally toward longitudinal ends and can be adjustably positioned vertically in relation to bottom wall 29, to provide the proper combination of access and stability; the side walls and side supports aid in preventing asymmetrical twisting of the yieldable body support 10 when held within the stabilizer 20.

The end walls 21, 22 and their support structure limit longitudinal by yielding; the side wall members 25 through 28, and their support structure, hold the yieldable body support 10 from sidewise movement; and the crosspieces 23 and 24 hold the body support 10 against undesirable vertical dislodgment.

As shown in FIG. 3, foundation structure for the stabilizer means includes strongbacks 32, 34 which hold together and support the various parts of the stabilizer means in fixed positional relationship. Strongbacks 32, 34 extend at least between longitudinal end walls 21, 22. In the embodiment shown, the end walls and the side walls are fixedly attached to the strongbacks as it is the bottom wall floor 29.

As best seen in FIG. 3, lateral side member 31 can include slots 36, 37 near its longitudinal ends for adjustment of its vertical position; slots (not shown) can be provided in the side wall members 26, 27 which can be used for adjusting placement of lateral side brace 31; similar provisions can also be made for side member 30 on the laterally opposite side of the stabilizer 20. Also, side braces 30, 31 can be provided with internally mounted padding.

Preferably, the strongbacks extend beyond longitudinal end walls as shown in FIG. 3 and include distal ends 40, 42 which are specially shaped. For example, beveled ends are provided which facilitate canting the stabilizer means 20 in a vertical plane as shown in FIG. 5. Such distal ends are covered with a commercially available non-skid material such as VELCRO. Also, such distal lends include apertures such as 46, 47, 48, 49 for suspending the entire structure. Cross beam races 50, 51, 52 are provided between strongbacks 33, 34 to provide added transverse strength.

FIGS. 4, 5 and 6 show the entire structure in various canted positions in relation to horizontal. In FIGS. 4 and 5, the structure is canted longitudinally with the strongbacks either being placed on a support 54, as shown in FIG. 4, or braced with distal ends against a wall and horizontal surface as shown in FIG. 5. The shaped distal ends of the strongbacks facilitate the canting positioning shown in FIG. 5.

In FIG. 6, the structure is canted laterally using the strongbacks on support 66. The variety of positions made available by the stabilizer structure facilitates working with a patient, not only for purposes of carrying out differing types of therapy, but also in providing for the beneficial results of changing attitudinal relationships.

As shown in FIG. 7, lengths of support chain 67, 68, 69, and 70 are attached to hardware at distal ends of the strongbacks and a support frame 72 so as to provide for swinging movement of a patient. Providing structure which enables various types of swinging movement is advantageous for various purposes including measuring improvement in the patient as a result of such movement.

The elongated body support 10 of FIG. 1 is preferably cut in one piece from foam rubber type materials, and is peripherally supported by stabilizer means 20.

The stabilizer means 20 can be molded, from commercially available engineering plastics of desired hardness and strength, in substantially one piece, allowing only, for example, for adjustment of the lateral side members such as 30, 31 or, the stabilizer means can be assembled from multiple pieces using, e.g. structural wood and plywood or fiberglass reinforced plastic pieces.

Typical wood and plywood pieces and dimensions for a specific embodiment of the configuration shown are listed below:

| Item | Material | Dimensions |
|---|---|---|
| Strongbacks 32, 34 | Structural wood | 50" length two by fours (2" × 4") with at least one end beveled |
| End walls 21, 22 | Plywood (up to ¾") | About 15" height, 12" transverse width |
| Cross beam braces 50, 51 52 | Structural wood | About 12" transverse length, 2" horizontal width |
| Side wall pieces 25-28 | Plywood (up to ¾") | About 15" height, about 2" at top with 18" base |
| Lateral side supports 30, 31 | Structural Hardwood | 36" length, about 5" width, up to ¾" thick |
| Bottom wall 29 | Plywood (up to ¾") | Overall length about 38", width about 12" (can be formed in two pieces) |

The elongated body support 10 is preferably covered with two-way stretch cotton fabric; medium density foamed vinyl is a preferred body cavity support material; such materials are well known and readily available commercially.

In the light of the above teachings, other materials, dimensions, and adaptations can be devised by those skilled in the art without departing from the concepts of the present invention; therefore, for purposes of determining the scope of the invention, reference should be made to the accompanying claims.

I claim:

1. Custodial protective structure for handling and therapeutic purposes for an individual subject to involuntary reflex responses, such as extensor thrust, comprising
    an elongated resiliently yieldable body support,
    such body support having a longitudinal axis and a centrally-located transverse axis, and defining a flexible body mold cavity which provides relaxed positioning over the full length of the body of an individual within such body support, such defined body cavity including
    a transverse concave portion for minimizing shoulder retraction,
    such concave portion being located for contact across the back at shoulder level of an individual within such defined body cavity, and
    stabilizing means for such body support including
    longitudinal end wall means for restraining and limiting longitudinal expansion of the defined body cavity,
    lateral support means extending between such longitudinal end wall means to prevent asymmetrical twisting of such yieldable body support about its longitudinal axis, and
    bottom support wall means for such body support.

2. The structure of claim 1 in which
    the stabilizing means includes
    elongated strongback means extending longitudinally the full length of such body support for holding the longitudinal end wall means in fixed positional relationship,
    such strongback means being located externally of such bottom wall means in relation to such body support and extending longitudinally beyond such longitudinal end wall means with such longitudinal extensions including preshaped distal ends for positioning such stabilizing means in canted relationship to vertical.

3. The structure of claim 2 in which such lateral support means include
    planar side wall members extending from longitudinal end wall means toward the centrally-located transverse axis,
    such side wall members decreasing in height in extending from such longitudinal end wall means toward such transverse axis.

4. The structure of claim 3 in which such lateral support means include
    side wall bracing members, and
    means for adjustably positioning such bracing members above such bottom wall means.

* * * * *